United States Patent [19]

Stryer et al.

[11] Patent Number: 4,542,104

[45] Date of Patent: Sep. 17, 1985

[54] PHYCOBILIPROTEIN FLUORESCENT CONJUGATES

[75] Inventors: Lubert Stryer, Stanford; Alexander N. Glazer, Orinda, both of Calif.

[73] Assignee: The Board of Trustees of the Leland Stanford Jr. Univ., Stanford, Calif.

[21] Appl. No.: 483,006

[22] Filed: Apr. 6, 1983

[51] Int. Cl.[4] .................. G01N 33/52; G01N 33/54
[52] U.S. Cl. .................................. 436/536; 436/537; 436/543; 436/544; 436/546; 436/800; 250/461.2
[58] Field of Search ............... 436/536, 537, 543, 544, 436/546, 800; 250/461.2

[56] References Cited

U.S. PATENT DOCUMENTS

| | | | |
|---|---|---|---|
| 4,199,559 | 4/1980 | Ullman et al. | 436/800 |
| 4,238,195 | 12/1980 | Boguslaski et al. | 436/800 |
| 4,261,968 | 4/1981 | Ullman et al. | 436/800 |
| 4,354,114 | 10/1982 | Karnaukhov et al. | 250/458.1 |
| 4,374,120 | 2/1983 | Soini et al. | 436/800 |

OTHER PUBLICATIONS

Troxler et al., Plant Physiol., 43 (1968) 1737–1739.
Köst-Reyes et al., Eur. J. Biochem., 102 (1979), pp. 83–91.

*Primary Examiner*—Christine M. Nucker
*Attorney, Agent, or Firm*—Bertram I. Rowland

[57] ABSTRACT

Fluorescent conjugates are employed providing combinations of a fluorescent sensitizer and a fluorescent phycobiliprotein. The conjugates find use in applications where large Stokes shifts, high absorption coefficients and high fluorescence quantum yields are desired. Particularly, combinations of phycobiliproteins are employed where the wavelength of excitation may be 50 nm or more different from the emission wavelength.

13 Claims, No Drawings

PHYCOBILIPROTEIN FLUORESCENT CONJUGATES

This work was supported by research grants from the National Institutes of Health (GM 24032) and the National Science Foundation (PCM 82-08158).

BACKGROUND OF THE INVENTION

1. Field of the Invention

There are many uses for fluorescent compounds or conjugates. Fluorescent compounds may be used as fluorescent labels for cell sorters, diagnostic assays, histology, fluorescence microscopy, immunocytochemical localization of antigenic markers, particularly for pathogens, and the like. The particular fluorescent label employed plays an important part in the sensitivity and accuracy of any particular methodology. In many situations, the sample which is involved has endogenous fluorescence which can provide for a substantial background. Other errors can be introduced through Rayleigh and Raman scattering. Many of these problems can be substantially alleviated, if not avoided, by having large Stokes shifts and emission at long wavelengths. The excitation light which is employed is at substantially shorter wavelengths from the emission light, so that the background light may be filtered out. It is therefore desirable to provide fluorescent labels which not only have high quantum efficiencies, so as to provide for intense signals, but also avoid the background error resulting from background fluorescence.

2. Description of the Prior Art

Properties of phycobiliproteins are described by Oi et al., *J. Cell Biol.* (1982) 93:981–986. Characteristics of phycobiliproteins may be found in Glazer and Hixson, *J. Biol. Chem.* (1977) 252:32–42 and Grabowski and Gantt, *Photochem. Photobiol.* (1978) 28:39–45. See also Lundell and Glazer, *J. Biol. Chem.* (1981) 256:12600–12606. Other references of interest are Glazer, 1981, in *The Biochemistry of Plants*, Hatch and Boardman, eds., Academic Press, New York 8:51–96, Bryant et al., *Arch. Microbiol.* (1976) 110:61–75 and Stryer, *Ann. Rev. Biochem.* (1978) 47:819–846. See particularly, Sigman et al., "The Evolution of Protein Structure and Function," 1980, Academic Press, N.Y., Glazer, In Structure and evolution of photosynthetic accessory pigment systems with special reference to phycobiliproteins, pp. 221-144.

SUMMARY OF THE INVENTION

Fluorescent conjugates are provided by employing combinations of fluorescers, where one of the fluorescers is a phycobiliprotein, and the emission spectrum of one of the fluorescers overlaps the absorption spectrum of the other. The conjugates provide for high absorption coefficients, high fluorescence quantum yields and large Stokes shifts and find particular application where fluorescent labels are employed and background fluorescence may be encountered.

DESCRIPTION OF SPECIFIC EMBODIMENTS

Novel fluorescent conjugates are provided, which are combinations of sensitizers (donors) and fluorescent compounds (acceptors), where one of the sensitizer and fluorescent compound is a phycobiliprotein. The sensitizer and fluorescent compound are related by a large overlap integral, so that energy is efficiently transferred from the sensitizer to the fluorescer. The energy donor is characterized by having a strong molar absorbence coefficient desirably greater than about $10^5$, preferably greater than about $10^6$ cm$^{-1}$M$^{-1}$. Desirably, the sensitizer should absorb light in the range of about 350–600 nm, more preferably in the range from about 400–600 nm, and transfer energy in the range of about 500–650 nm, usually in the range of about 500–625 nm. The acceptor molecule will generally absorb light in the range of about 400–600 nm, and emit light in the range of about 450–700 nm, preferably in the range of about 500–700 nm. The excitation energy maximum of the donor and the emission maximum of the fluorescer will be separated by at least about 15 nm, usually at least about 25 nm and preferably by at least about 50 nm, and may be as large a separation as 80 nm or greater. The donor-acceptor pair should have a spectral overlap integral of at least about $10^{-16}$ cm$^3$M$^{-1}$.

Usually, there will be at least 10% efficiency of transfer at a distance of from about 1–10 nm between chromophoric groups, preferably at least about 50% efficiency of transfer and more preferably 50% efficiency of transfer at from about 3–10 nm, more usually from about 4–8 nm.

The donor molecule may be a wide variety of molecules which absorb light at or above 350 nm and emit light at or above 400 nm. These molecules can be fluorescein and its derivatives, umbelliferone or its derivatives, rhodopsins, metalloproteins, europium metal chelates, porphyrins, etc. Depending upon their absorption and emission characteristics, various phycobiliproteins can be used as donors or acceptors. These phycobiliproteins may be allophycocyanin, allophycocyanin B, C-phycocyanin, R-phycocyanin, C-phycoerythrin, B-phycoerythrin, B-phycoerythrin I and II, and the like. The phycobiliproteins may be obtained from various species of cyanobacteria (blue-green algae), red algae and cryptomonads.

The donors and acceptors may be either large or small molecules. Particularly, low molecular weight donors may be employed which have molecular weights in the range of about 250 to 2000. Alternatively, large fluorescent molecules may be employed, particularly proteins which may range in mass from about 10 kd (kilodaltons) to about 600 kd or more. In some instances subunits of the phycobiliproteins may find use, the subunits ranging from greater than 5 kd to 50 kd in mass.

The donor and acceptor molecules may be joined in a variety ways, both covalently and non-covalently. Covalent coupling can involve the direct bonding of functionalities present on the donor and acceptor molecules or introducing a linking group. The linking groups generally having a chain of fewer than about 12 atoms in the chain, more usually fewer than 8, and generally having from about 1–6 atoms, which are carbon, nitrogen, oxygen and sulfur.

The fluorescent compositions of this invention can be used as a single composite fluorescer, so as to provide for the high efficiency and high Stokes shift provided by the fluorescent combination or can be used separately, whereby virtue of the particular application, the two components are brought together into energy transfer relationship.

Where the two components are covalently joined, a wide variety of linking groups can be employed for covalent bonding. Where the two components are proteins, bifunctional reagents may be employed, where the reagents are the same or different. Illustrative reagents include glutaraldehyde, bis-didiazobiphenyl, maleimidoacetic acid NHS ester, methyldithioacetic acid NHS ester, 3-(2'-pyridylthio)-propionic acid NHS ester, etc. (NHS-N-hydroxysuccinimdyl; other esters may also be used, such as p-nitrophenyl). For non-covalent bonding, various polyvalent receptors can be employed or combinations of receptors and ligands, such as antibodies, biotin-avidin, F(ab')$_2$, naturally occurring receptors, and the like.

For a list of phycobiliproteins and their spectral properties see U.S. application Ser. No. 309,169, filed Oct. 6, 1981, now abandoned and refiled as Ser. No. 454,768, now U.S. Pat. No. 4,520,110, which application is incorporated herein by reference.

The subject donor-acceptor fluorescer compounds may be conjugated as labels to a wide variety of molecules. These conjugates may be used in a wide variety of ways, enhancing known methodologies for the detection, diagnosis, measurement and study of antigens and receptors, either present as individual molecules, or in more complex organizations, such as viruses, cells, tissue, organelles, e.g. plastids, nuclei, etc.

One of the uses of the subject conjugates is in fluorescent staining of cells. The cells may then be observed under a microscope, the presence of the fluorescent conjugate being diagnostic of the presence of a specific determinant site. Alternatively, the conjugates may be used for the detection, separation or other application in a fluorescence activated cell sorter.

Another use of the subject conjugates is in diagnostic assays, such as immunoassays or competitive protein binding assays, where the fluorescence emission may be measured at much higher wavelengths. Here, the donor-acceptor pair may be conjugated to either a ligand or a receptor, particularly an antibody. While for the most part, the antibodies will be IgG, other antibodies such as IgA, IgD, IgE and IgM may also find use, as well as fragments of the immunoglobulins.

In addition, various naturally occurring receptors may be employed, particularly receptors having high binding specificity, such as avidin. By biotinylating either the receptor, the donor-acceptor conjugate or both, one can link various molecules through avidin.

A wide variety of fluorescent assays are known. A few of these assays are illustrated in U.S. Pat. Nos. 3,998,943; 3,985,867; 3,996,345, 4,036,946; 4,067,959; 4,160,016; and 4,166,105, the relevant portions of which are incorporated herein by reference.

The subject donor-acceptor conjugates have the favorable properties of the biliproteins, such as (1) high absorption coefficients in the longer wavelength visible spectral regions; (2) high fluorescence quantum yields; (3) long term stability, including good storage stability; (4) high water solubility; (5) ease of coupling to other molecules; and (6) low non-specific binding, as well as the additional property of having a large Stokes shift, so that background fluorescence is substantially diminished and one can observe fluorescence at very long wavelengths with little background interference resulting from scattering, fluorescence of normally encountered materials in samples, and the like. There is the further advantage that it is easier to work in the red end of the spectrum, rather than in the ultraviolet region, because plastic materials do not absorb and emit in the yellow to red spectral region.

Where the two components are used separately on separate components, it is necessary to provide that the donor and acceptor be brought together into close spatial proximity. This will normally be achieved by conjugating the two components to members of specific binding pairs, such as ligands and receptors. Thus, one could conjugate one component to an antigen and the other component to a receptor for the antigen or the two components of the fluorescent combination may be conjugated to different receptor molecules for the same antigen. The method of conjugation must allow for the bringing together of the two components of the donor-acceptor fluorescent composition into energy transfer distances. Therefore, compositions will be provided which involve ligand (either hapten or antigen)-component-(1) conjugate and receptor-component-(2) conjugate or antiligand-component-(1) and antiligand-component-(2), where the two antiligands are for the same ligand, but at least in part will bind to different determinant sites. In some situations it may be desirable that the conjugates be to the antiligand, so as to form large complexes or three-dimensional aggregations with high localized concentrations of the two components of the fluorescent composition.

The following examples are offered by way of illustration and not by way of limitation:

EXPERIMENTAL

Materials and Methods

Preparation of B-Phycoerythrin-Allophycocyanin Conjugate

Reaction of B-phycoerythrin with SPDP. To 1.0 ml (12.7 mg) of *Phorphyridium cruentum* B-phycoerythrin (Glazer and Hixson (1977) supra) in 0.1 M NaCl, pH 7.4, was added 10 µl (0.165 mg) N-succinimidyl 3-(2'-pyridylthio)propionate (SPDP) in anhydrous methanol. After 70 min, the reaction mixture was applied to a column of Sephadex G-25 (1.0×25 cm), equilibrated, and eluted with 0.1 M Na-phosphate—0.1 M NaCl, pH 7.4. The frontally eluted B-phycoerythrin-S-S-pyridyl derivative was stored at 4°.

Preparation of Thiolated Allophycocyanin. To 0.38 ml (6 mg) of *Anabaena variabilis* allophycocyanin (Bryant et al., *Arch. Microbiol.* (1976) 110:61–75) in 0.1 M Na-phosphate—0.1 M NaCl, pH 7.4, was added 10 µl (0.169 mg) of SPDP in anhydrous methanol. After 60 min, the reaction was terminated by the addition of 20 µl 1 M dithiothreitol in the pH 7.4 buffer. After a further 30 min, the reaction mixture was applied to a column of Sephadex G-25 (1.0×30 cm) and eluted with 0.1 M Na-phosphate—0.1 M NaCl, pH 7.4. Thiolated allophycocyanin was used immediately after gel filtration.

Spectroscopic Properties of the Modified Biliproteins. Both the absorption and fluorescence emission spectra of the B-phycoerythrin-S-S-pyridyl adduct and of thiolated allophycocyanin were the same as those of the unmodified proteins.

Conjugation Reaction. Thiolated allophycocyanin (2.52 mg, in 0.7 ml 0.1 M Na-phosphate—0.1 M NaCl, pH 7.4) was mixed with the B-phycoerythrin-S-S-pyridyl derivative (5.12 mg, in 0.7 ml of the same buffer). After 18 h, the reaction mixture was dialyzed against 100 ml 0.1 M NaCl at room temperature for 180 min.

Purification of the B-Phycoerythrin-Allophycocyanin Conjugate. The dialyzed reaction mixture was applied to a column of hydroxyapatite (5 ml settled bed volume) equilibrated with 0.001 M Na-phosphate—0.1 M NaCl, pH 7.3. The column was washed with 20 ml of starting buffer, and then developed with 20 mM Na-phosphate—0.09 M NaCl, pH 7.3. This eluted a well-defined phycoerythrin zone. Elution with this buffer was continued until a barely detectable pink color remained in the eluate. At this point, the purple conjugate was eluted with 0.05 M NaCl—0.1 M Na-phosphate, pH 7.3. The molarity of B-phycoerythrin and of allophycocyanin in this column fraction was $4.25 \times 10^{-6}$ M and $6.88 \times 10^{-6}$ M, respectively, i.e. a molar ratio of allophycocyanin to phycoerythrin of 1.62. High-pressure liquid chromatography on a Waters instrument with a Varian G3000SW gel filtration column showed that column fractions containing the phycoerythrin-allophycocyanin conjugate were devoid of free phycoerythrin. The conjugate was used without further purification.

Spectroscopic measurements. Absorption spectra were obtained on a Beckman model 25 spectrophotometer. Fluorescence spectra were obtained on a Perkin-Elmer model 44B fluorimeter equipped with a DCSCU-2 corrected emission spectra unit, or on a Spex Fluorolog instrument. The emission spectra reported here are nominally corrected spectra obtained with the Perkin-Elmer fluorimeter. Nanosecond emission kinetics were measured with a single-photon counting apparatus employing a mode-locked argon-ion laser with a synchronously pumped rhodamine 6G dye laser as the excitation source.

The absorption spectrum of the conjugate was found to be the sum of the contributions of the phycoerythrin and allophycocyanin components. The fluorescence emission spectrum of the conjugate excited at 500 nm showed a phycoerythrin contribution peaked at 576 nm and an allophycocyanin contribution peaked at 660 nm. The intensity of phycoerythrin fluorescence from the conjugate was 10% of that obtained from an equimolar concentration of phycoerythrin alone. The excitation spectrum of the 660 nm fluorescence of the conjugate showed that the phycoerythrin fluorescence in the conjugate was quenched 90%, because of highly efficient energy transfer to allophycocyanin. Only 5% of the 660 nm emission of the conjugate excited at 500 nm arises from direct excitation of the allophycocyanin component. Nearly all of the 660 nm emission of the conjugate is sensitized fluorescence.

To demonstrate the effect of cleavage of the disulfide bond on the energy transfer, the conjugate was introduced into a solution of 50 mM dithiothreitol. As the reduction proceeded, the 660 nm of allophycocyanin decreased and the 576 nm emission of phycoerythrin increased. On reaching a plateau value in 2 h, the phycoerythrin emission intensity of the dithiothreitol-treated conjugate was nearly the same as that of an equimolar solution of native phycoerythrin.

Nanosecond emission kinetics were determined, where the excited state lifetime of the phycoerythrin emission of the conjugate is less than 0.3 nsec, compared with 2.1 nsec for free phycoerythrin. There was no detectable 2.1 nsec component in the emission of the conjugate. Following the addition of dithiothreitol, the amplitude of the $\tau = 2.1$ nsec component of the emission increases at the same rate as the increase in 576 nm fluorescence intensity. The spectroscopic properties of phycoerythrin and allophycocyanin are as follows. Phycoerythrin has an absorption coefficient of $2.4 \times 10^6$ cm$^{-1}$M$^{-1}$ arrising from 40 bilin chromophores. Phycoerythrin has a quantum yield of $Q = 0.98$ and its spectral overlap integral with allophycocyanin is $J = 6.95 \times 10^{-13}$ cm$^3$M$^{-1}$ in Förster's equation for dipole-dipole transfer. This calculation of J is for transfer from phycoerythrin to a single allophycocyanin chromophore with $\epsilon = 1.05 \times 10^5$ cm$^{-1}$ M$^{-1}$ at 650 nm. For $n = 1.4$ and $K^2 = 0.67$, the calculated $R_o$ distance for 50% transfer between a terminal phycoerythrin chromophore and a single allophycocyanin chromophore is 6.8 nm.

Allophycocyanin has intensive absorption from about 470 to 650 nm and an emission peak at 660 nm.

The subject conjugates provide for a number of advantages. The wide separation between wavelengths of strong absorption and emission can be exploited in fluorescence immunoassays and other analyses to reject Rayleigh and Raman scattering. Also, with the subject conjugates, several compounds with different emission spectra can be simultaneously excited with high efficiency at a single excitation wavelength. This means that analyses for two or more components can be simultaneously carried out with a single excitation beam. For example, a multiparameter fluorescence-activated cell sorter using a series of tandem conjugates according to this composition could be employed. Immunocytochemical localization of several antigen markers could be performed by fluorescence microscopy employing the subject conjugates. The retention of the favorable absorption and emission properties of the subject compositions employing one or two phycobiliproteins, following conjugation to each other or to other molecules indicates that they have broad applicability in fluorescence analyses of molecules and cells.

Although the foregoing invention has been described in some detail by way of illustration and example for purposes of clarity of understanding, it will be obvious that certain changes and modifications may be practiced within the scope of the appended claims.

What is claimed is:

1. A conjugate comprising an energy donor as a first component and a fluorescer as a second component joined together at an energy exchanging distance, wherein one of said first and second components is a phycobiliprotein and the two components have a spectral overlap integral of at least about $10^{-16}$ cm$^3$M$^{-1}$.

2. A conjugate according to claim 1, wherein said first and second components are phycobiliproteins.

3. A conjugate according to claim 2, wherein said phycobiliproteins are covalently joined by a linking group wherein said first and second components are separated by not more than 10 nm.

4. A conjugate according to claim 3, wherein a portion of said linking group is a disulfide linkage.

5. A conjugate according to claim 1, wherein said fluorescer fluoresces at a wavelength in the range of about 550 to 800 nm.

6. A conjugate according to claim 1, wherein said first and second components are covalently joined.

7. A conjugate comprising two phycobiliproteins joined within energy exchanging distance, wherein one of said phycobiliproteins absorbs light in the range of about 300 to 600 nm and emits light in the range of about 400 to 700 nm and the other of said phycobiliproteins absorbs light in the range of about 400 to 650 nm and emits light in the range of about 500 to 800 nm, wherein there is substantial overlap between the emission spectrum of one and the absorption spectrum of the other to provide a spectral overlap integral of at least about $10^{-16}$ cm$^3$M$^{-1}$.

8. A conjugate according to claim 7, wherein one of said phycobiliproteins is phycoerythrin and the other of said phycobiliproteins is allophycocyanin.

9. A conjugate according to claim 8, wherein said phycobiliproteins are joined by a linking group containing a disulfide linkage.

10. A conjugate comprising an energy donor-acceptor pair according to claim 1 covalently joined to a ligand or receptor.

11. In a cell staining, fluorescence-activated cell sorting or competitive protein binding diagnostic assay method employing a fluorescent label, where a labeled ligand and/or receptor are brought together and fluorescence is detected in relation to the binding of said ligand and receptor, the improvement comprising employing the conjugate composition according to claim 1 as the fluorescent label.

12. A method according to claim 11, wherein said method is fluorescence activated cell sorting.

13. A method according to claim 11, wherein said method is a diagnostic assay employing a fluorescent label.

* * * * *